US008029747B2

(12) United States Patent
Helmerson

(10) Patent No.: US 8,029,747 B2
(45) Date of Patent: Oct. 4, 2011

(54) PRESSURE EQUALIZING DEVICE, RECEPTACLE AND METHOD

(75) Inventor: Elisabet Helmerson, Billdal (SE)

(73) Assignee: Carmel Pharma AB, Göteborg (SE)

( * ) Notice: Subject to any disclaimer, the term of this patent is extended or adjusted under 35 U.S.C. 154(b) by 330 days.

(21) Appl. No.: 11/762,550

(22) Filed: Jun. 13, 2007

(65) Prior Publication Data

US 2008/0311007 A1 Dec. 18, 2008

(51) Int. Cl.
*A61M 5/00* (2006.01)

(52) U.S. Cl. ........ 422/546; 422/500; 422/501; 422/513; 422/544; 422/939; 422/946; 604/405; 604/411; 604/412; 604/413; 604/414; 604/415; 604/416; 141/329; 141/330; 222/397; 222/399

(58) Field of Classification Search .......... 422/102–104, 422/939–948, 500, 501, 513, 544, 546; 604/405, 604/411–416; 141/329, 330; 222/397, 399
See application file for complete search history.

(56) References Cited

U.S. PATENT DOCUMENTS

| | | | |
|---|---|---|---|
| 1,844,342 | A | 2/1932 | Berman |
| 2,010,417 | A | 8/1935 | Schwab |
| 2,697,438 | A | 12/1954 | Hickey |
| 2,717,599 | A | 9/1955 | Huber |
| 3,064,651 | A | 11/1962 | Henderson |
| 3,071,135 | A | 1/1963 | Baldwin et al. |
| 3,308,822 | A | 3/1967 | DeLuca |
| 3,316,908 | A | 5/1967 | Burke |
| 3,340,671 | A | 9/1967 | Loo |
| 3,390,677 | A | 7/1968 | Razimbaud |
| 3,448,740 | A | 6/1969 | Figge |
| 3,542,240 | A | 11/1970 | Solowey |
| 3,783,895 | A | 1/1974 | Weichselbaum |
| 3,788,320 | A | 1/1974 | Dye |
| 3,822,700 | A | 7/1974 | Pennington |
| 3,938,520 | A | 2/1976 | Scislowicz et al. |
| 3,976,073 | A | 8/1976 | Quick et al. |

(Continued)

FOREIGN PATENT DOCUMENTS

AU 200112863 5/2003

(Continued)

OTHER PUBLICATIONS

Taiwan Search Report for Taiwan Patent Application 092106323 dated Mar. 21, 2003 (4 pages).

(Continued)

*Primary Examiner* — Jill Warden
*Assistant Examiner* — Shogo Sasaki
(74) *Attorney, Agent, or Firm* — Fish & Richardson P.C.

(57) ABSTRACT

Pressure equalizing device comprising a fluid container for attachment to a receptacle such as a vial to permit pressure equalization between the fluid container and the receptacle. The pressure equalizing device comprises a flow channel that is arranged to provide fluid communication into or out of the fluid container when the pressure equalizing device is attached to the receptacle. The pressure equalizing device also comprises a fluid inlet that contains a one-way valve that permits fluid to flow into the fluid container via said fluid inlet and that prevents fluid from flowing out of the fluid container via said fluid inlet and filter-receiving means that are arranged to permit fluid flowing into or out of the fluid container to be filtered when the filter-receiving means comprises a filter.

14 Claims, 7 Drawing Sheets

U.S. PATENT DOCUMENTS 4,096,860 A 6/1978 McLaughlin
4,296,786 A 10/1981 Brignola
D270,568 S 9/1983 Armstrong
4,490,139 A 12/1984 Huizenga et al.
4,516,967 A 5/1985 Kopfer
4,564,054 A 1/1986 Gustavsson
4,573,967 A 3/1986 Hargrove et al.
4,576,211 A 3/1986 Valentini et al.
4,581,016 A 4/1986 Gettig
4,582,223 A 4/1986 Kobe
4,588,403 A 5/1986 Weiss et al.
4,600,040 A 7/1986 Naslund
4,623,343 A 11/1986 Thompson
4,629,455 A 12/1986 Kanno
4,632,673 A 12/1986 Tiitola et al.
4,636,204 A 1/1987 Christopherson et al.
4,673,400 A 6/1987 Martin
4,673,404 A 6/1987 Gustavsson
4,737,150 A 4/1988 Baeumle et al.
4,752,287 A 6/1988 Kurtz et al.
4,759,756 A 7/1988 Forman et al.
4,768,568 A 9/1988 Fournier et al.
4,792,329 A 12/1988 Schreuder
4,804,015 A 2/1989 Albinsson
4,822,340 A 4/1989 Kamstra
4,826,492 A 5/1989 Magasi
4,834,717 A 5/1989 Haber et al.
4,842,585 A 6/1989 Witt
4,850,978 A 7/1989 Dudar et al.
4,864,717 A 9/1989 Baus, Jr.
4,872,494 A 10/1989 Coccia
4,878,897 A 11/1989 Katzin
4,889,529 A 12/1989 Haindl
4,898,209 A 2/1990 Zbed
4,909,290 A 3/1990 Coccia
4,932,937 A 6/1990 Gustavsson et al.
4,944,736 A 7/1990 Holtz
4,964,855 A 10/1990 Todd et al.
4,982,769 A 1/1991 Fournier et al.
4,994,048 A 2/1991 Metzger
4,997,083 A 3/1991 Loretti et al.
5,017,186 A 5/1991 Arnold
5,041,105 A 8/1991 D'Alo et al.
5,061,264 A 10/1991 Scarrow
5,071,413 A 12/1991 Utterberg
5,122,116 A 6/1992 Kriesel et al.
5,122,123 A 6/1992 Vaillancourt
5,137,524 A 8/1992 Lynn et al.
5,158,554 A 10/1992 Jepson et al.
5,176,673 A 1/1993 Marrucchi
5,199,947 A 4/1993 Lopez et al.
5,201,725 A 4/1993 Kling
5,207,658 A 5/1993 Rosen et al.
5,232,109 A 8/1993 Tirrell et al.
5,254,097 A 10/1993 Schock et al.
5,279,576 A 1/1994 Loo et al.
5,279,583 A 1/1994 Shober, Jr. et al.
5,279,605 A 1/1994 Karrasch et al.
5,308,347 A 5/1994 Sunago et al.
5,312,366 A 5/1994 Vaillancourt
5,328,480 A 7/1994 Melker et al.
5,334,163 A 8/1994 Sinnett
5,356,406 A 10/1994 Schraga
5,385,545 A 1/1995 Kriesel et al.
5,385,547 A 1/1995 Wong et al.
5,389,085 A 2/1995 D'Alessio et al.
5,405,326 A 4/1995 Haber et al.
5,445,630 A 8/1995 Richmond
5,447,501 A 9/1995 Karlsson et al.
5,456,675 A 10/1995 Wolbring et al.
5,470,522 A 11/1995 Thome et al.
5,478,328 A 12/1995 Silverman et al.
5,478,337 A 12/1995 Okamoto et al.
5,492,531 A 2/1996 Post et al.
5,514,117 A 5/1996 Lynn
5,515,871 A 5/1996 Bittner et al.
5,536,259 A 7/1996 Utterberg
5,575,780 A 11/1996 Saito
5,593,028 A 1/1997 Haber et al.
5,613,954 A 3/1997 Nelson et al.
5,632,735 A 5/1997 Wyatt et al.
5,647,845 A 7/1997 Haber et al.
5,685,866 A 11/1997 Lopez
5,752,942 A 5/1998 Doyle et al.
5,766,147 A 6/1998 Sancoff et al.
5,766,211 A 6/1998 Wood et al.
5,782,872 A 7/1998 Muller
5,795,336 A 8/1998 Romano et al.
5,817,083 A 10/1998 Shemesh et al.
5,820,609 A 10/1998 Saito
5,827,262 A 10/1998 Neftel et al.
5,837,262 A 11/1998 Golubev et al.
5,875,931 A 3/1999 Py
5,879,345 A 3/1999 Aneas
5,897,526 A 4/1999 Vaillancourt
5,934,510 A 8/1999 Anderson
5,984,899 A 11/1999 D'Alessio et al.
6,063,068 A 5/2000 Fowles et al.
D427,308 S 6/2000 Zinger
6,070,623 A 6/2000 Aneas
6,071,270 A 6/2000 Fowles et al.
6,090,091 A 7/2000 Fowles et al.
6,113,068 A 9/2000 Ryan
6,113,583 A 9/2000 Fowles et al.
6,142,446 A 11/2000 Leinsing
6,146,362 A 11/2000 Turnbull et al.
6,209,738 B1 4/2001 Jansen et al.
6,221,065 B1 4/2001 Davis
6,245,056 B1 6/2001 Walker et al.
D445,501 S 7/2001 Niedospial, Jr.
6,253,804 B1 7/2001 Safabash
6,258,078 B1 7/2001 Thilly
6,387,074 B1 5/2002 Horppu et al.
6,453,956 B2 9/2002 Safabash
6,471,674 B1 10/2002 Emig et al.
6,517,523 B1 2/2003 Kaneko et al.
6,537,263 B1 3/2003 Aneas
6,571,837 B2 6/2003 Jansen et al.
6,591,876 B2 7/2003 Safabash
6,644,367 B1 11/2003 Savage et al.
6,685,692 B2 2/2004 Fathallah
6,715,520 B2 4/2004 Andreasson et al.
6,761,286 B2 7/2004 Py et al.
D495,416 S 8/2004 Dimeo et al.
6,786,244 B1 9/2004 Jones
D506,256 S 6/2005 Miyoshi et al.
6,960,194 B2 11/2005 Hommann et al.
7,000,806 B2 2/2006 Py et al.
7,080,672 B2 7/2006 Fournier et al.
7,297,140 B2 11/2007 Orlu et al.
D570,477 S 6/2008 Gallogly et al.
D572,820 S 7/2008 Gallogly et al.
D577,438 S 9/2008 Gallogly et al.
D577,822 S 9/2008 Gallogly et al.
D582,033 S 12/2008 Baxter et al.
D605,755 S 12/2009 Baxter et al.
7,703,486 B2 4/2010 Costanzo
D616,984 S 6/2010 Gilboa
7,744,581 B2 6/2010 Wallen et al.
2001/0021825 A1 9/2001 Becker et al.
2001/0025671 A1 10/2001 Safabash
2002/0002352 A1 1/2002 Becker et al.
2002/0082586 A1 6/2002 Finley et al.
2002/0127150 A1 9/2002 Sasso
2002/0177819 A1 11/2002 Barker et al.
2003/0010717 A1 1/2003 Brugger et al.
2003/0070726 A1* 4/2003 Andreasson et al. ......... 141/329
2003/0106610 A1 6/2003 Roos et al.
2003/0107628 A1 6/2003 Fowles et al.
2003/0199846 A1 10/2003 Fowles et al.
2003/0233083 A1 12/2003 Houwaert et al.
2004/0116858 A1 6/2004 Heinz et al.
2004/0199139 A1 10/2004 Fowles et al.
2004/0215147 A1* 10/2004 Wessman et al. ............. 604/187
2005/0215977 A1 9/2005 Uschold
2006/0025747 A1 2/2006 Sullivan et al.
2006/0106360 A1* 5/2006 Wong ............................ 604/411

| | | | | |
|---|---|---|---|---|
| 2006/0111667 | A1 | 5/2006 | Matsuura et al. | |
| 2006/0157984 | A1 | 7/2006 | Rome et al. | |
| 2006/0186045 | A1 | 8/2006 | Jensen et al. | |
| 2007/0021725 | A1 | 1/2007 | Villette | |
| 2007/0060841 | A1 | 3/2007 | Henshaw | |
| 2007/0088313 | A1 | 4/2007 | Zinger et al. | |
| 2007/0106244 | A1 | 5/2007 | Mosler et al. | |
| 2007/0179441 | A1 | 8/2007 | Chevallier | |
| 2007/0270759 | A1 | 11/2007 | Pessin | |
| 2007/0270778 | A9 | 11/2007 | Zinger et al. | |
| 2008/0045919 | A1 | 2/2008 | Jakob et al. | |
| 2008/0103453 | A1 | 5/2008 | Liversidge | |
| 2008/0103485 | A1 | 5/2008 | Kruger | |
| 2008/0172039 | A1 | 7/2008 | Raines | |
| 2008/0223484 | A1 | 9/2008 | Horppu | |
| 2008/0287920 | A1 | 11/2008 | Fangrow et al. | |
| 2008/0312634 | A1 * | 12/2008 | Helmerson et al. ........... | 604/414 |
| 2009/0254042 | A1 | 10/2009 | Gratwohl et al. | |
| 2010/0137827 | A1 | 6/2010 | Warren et al. | |
| 2010/0204671 | A1 | 8/2010 | Kraushaar et al. | |
| 2010/0243099 | A1 | 9/2010 | Yodfat | |

FOREIGN PATENT DOCUMENTS

| | | |
|---|---|---|
| DE | 2005519 | 10/1979 |
| EP | 0255025 | 2/1988 |
| EP | 0259582 | 3/1988 |
| EP | 0285424 | 10/1988 |
| EP | 0311787 | 4/1989 |
| EP | 0376629 | 7/1990 |
| EP | 0803267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| GB | 1579065 | 11/1980 |
| JP | 49-12690 | 5/1972 |
| JP | 288664 | 7/1990 |
| JP | 3030963 | 8/1996 |
| JP | 2000167022 | 6/2000 |
| JP | 2001505092 | 4/2001 |
| JP | 2001293085 | 10/2001 |
| TW | 482670 | 4/2002 |
| WO | WO 84/04672 | 12/1984 |
| WO | WO 84/04673 | 12/1984 |
| WO | WO 90/03536 | 4/1990 |
| WO | WO 98/19724 | 5/1998 |
| WO | WO 99/27886 | 6/1999 |
| WO | WO 99/62578 | 12/1999 |
| WO | WO 00/05292 | 2/2000 |
| WO | WO 00/35517 | 6/2000 |
| WO | WO 01/80928 | 11/2001 |
| WO | WO 02/02048 | 1/2002 |
| WO | WO 02/11794 | 2/2002 |
| WO | WO 02/064077 | 8/2002 |
| WO | WO 02/076540 | 10/2002 |
| WO | WO 2005/074860 | 8/2005 |
| WO | WO 2006/082350 | 8/2006 |
| WO | WO 2006/083333 | 8/2006 |
| WO | WO 2006/138184 | 12/2006 |
| WO | WO 2008/115102 | 9/2008 |

OTHER PUBLICATIONS

Japan Application No. 2003-583539, Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009 (2 pages).

* cited by examiner

PRESSURE EQUALIZING DEVICE, RECEPTACLE AND METHOD

TECHNICAL FIELD

The present invention concerns a pressure equalizing device comprising a fluid container, i.e. liquid and/or gas container, for attachment to a receptacle, such as a vial, to permit pressure equalization between the fluid container and the receptacle. The present invention also concerns a receptacle comprising such a pressure equalizing device.

BACKGROUND OF THE INVENTION

When preparing and administering drugs care has be taken to minimize, or preferably eliminate the risk of exposing people, such as medical and pharmacological personnel, to toxic substances. Safety boxes, cabinets or isolators are often used to prepare drugs to reduce the risk of toxic substances leaking into breathable air. However, such facilities require a lot of space, they are non-portable and can be expensive to install, maintain and repair.

Some drugs must be dissolved or diluted before they are administered, which involves transferring a solvent from one container to a sealed vial containing the drug in powder or liquid form, by means of a needle for example. Drugs may be inadvertently released into the atmosphere in gas form or by way of aerosolization, during the withdrawal of the needle from the vial and while the needle is inside the vial if any pressure differential between the interior of the vial and surrounding atmosphere exists.

This problem may be eliminated or at least minimized by using a pressure equalization device that may be attached to a vial during the preparation of drugs. The pressure equalization device comprises a gas container in communication with the interior of the vial, which ensures that neither an increased pressure nor a vacuum can occur inside the vial when gas or liquid is injected into or withdrawn from the vial. The gas container may be filled with cleaned or sterilized air prior to its use to ensure that the contents of the vial do not become contaminated with air-borne particles such as dust, pollen, mould or bacteria and other undesirable substances.

SUMMARY OF THE INVENTION

An object of the present invention is to provide an improved pressure equalizing device comprising a fluid container, i.e. gas and/or liquid container, for attachment to a receptacle, such as a vial, to permit pressure equalization between the fluid container and the receptacle.

This object is achieved by a pressure equalizing device comprising the features of claim 1, which comprises a fluid container and a flow channel that is arranged to provide fluid communication into or out of the fluid container when the pressure equalizing device is attached to the receptacle. The pressure equalizing device also comprises a fluid inlet that contains a one-way valve that permits fluid to flow into the fluid container via said fluid inlet and that prevents fluid from flowing out of the fluid container via said fluid inlet. The pressure equalizing device also comprises filter-receiving means that are arranged to permit fluid flowing into or out of the fluid container to be filtered when the filter-receiving means comprises a filter.

The pressure equalizing device equalizes pressure in the fluid container and the receptacle by allowing filtered fluid to flow into or out of the receptacle (depending on whether the pressure is temporarily greater in the fluid container or the receptacle). The pressure equalizing device thereby provides a simple, closed system that allows for safe and reliable injection or withdrawal of substances, such as toxic drugs, into or out of a receptacle while at least minimizing, or eliminating the risk of the substances contaminating breathable air.

According to an embodiment of the invention the filter-receiving means comprises a removable or non-removable filter. As an example, a filter with the mesh size 0.2 μm may be used to remove substantially all particles and micro organisms of that size or larger. The filter may be a sterilizing or aseptisizing filter, such as a particulate air filter, such as a high efficiency particulate air (HEPA) filter to remove gas-borne particles such as dust, pollen, mould or bacteria and thus eliminating or at least reducing the risk of such gas-borne particles from contaminating substances inside the vial. It should be noted that the pressure equalizing device may comprise a plurality of filters of the same type or of different types.

According to an embodiment of the invention the filter-receiving means are located upstream or downstream of the one-way valve in the fluid inlet, which permits fluid to be filtered as it flows into the fluid container when the filter-receiving means comprises a filter. According to another embodiment of the invention the filter-receiving means are located in the flow channel, which permits fluid to be filtered as it flows out of the fluid container into the receptacle when the filter-receiving means comprises a filter.

According to a further embodiment of the invention the fluid container is an air container.

According to another embodiment of the invention the fluid inlet is arranged to be in communication with ambient, i.e. non-sterilized air. Since ambient air can be cleaned on site using a sterilizing or ascepticizing filter in the pressure equalizing device, neither a sterile environment, nor extra equipment, nor a supply of clean air is necessary to fill the fluid container with cleaned air. The pressure equalizing device according to the present invention may therefore be filled or replenished with cleaned fluid almost anywhere, in a simple manner and at low cost.

According to a further embodiment of the invention the fluid container comprises a flexible portion, such as a bladder, i.e. a portion comprising a flexible or expandable material, whereby the volume of said portion can be increased by drawing fluid into the fluid container and decreased by withdrawing fluid from the fluid container. The fluid container may however be at least partly constituted of a rigid, non-compressible material.

According to an embodiment of the invention the one-way valve is integrally formed with the filter-receiving means or a filter.

According to another embodiment of the invention the filter-receiving means is removable from the fluid container.

According to a further embodiment of the invention the pressure equalizing device comprises connecting means, such as a bayonet coupling, luer lock or snap fit mechanism, for attachment of the pressure equalizing device to an injector such as a syringe and/or connecting means, such as a snap fit mechanism for attachment of the pressure equalizing device to a receptacle.

According to an embodiment of the invention at least part of the fluid container is integrally formed with the connecting means, from the same material for example, whereby the material may be a thermoplastic material, such as polyethylene or polypropylene; acrylonitrile butadiene styrene (ABS), polycarbonate, polyester or any other suitable material.

According to another embodiment of the invention the fluid container is detachable from the connecting means.

The present invention also concerns a receptacle that comprises a pressure equalizing device according to any of the embodiments of the invention.

According to an embodiment of the invention at least part of the pressure equalizing device is integrally formed with at least one component of the receptacle, such as its cap or sealing means.

The pressure equalizing device according to the present invention is intended particularly, but not exclusively for use as a pressure equalizing device during the preparation or administration of drugs.

BRIEF DESCRIPTION OF THE DRAWINGS

The present invention will hereinafter be further explained by means of non-limiting examples with reference to the appended figures where.

It should be noted that the drawings have not been drawn to scale and that the dimensions of certain features have been exaggerated for the sake of clarity.

DETAILED DESCRIPTION OF EMBODIMENTS

Figure 1:
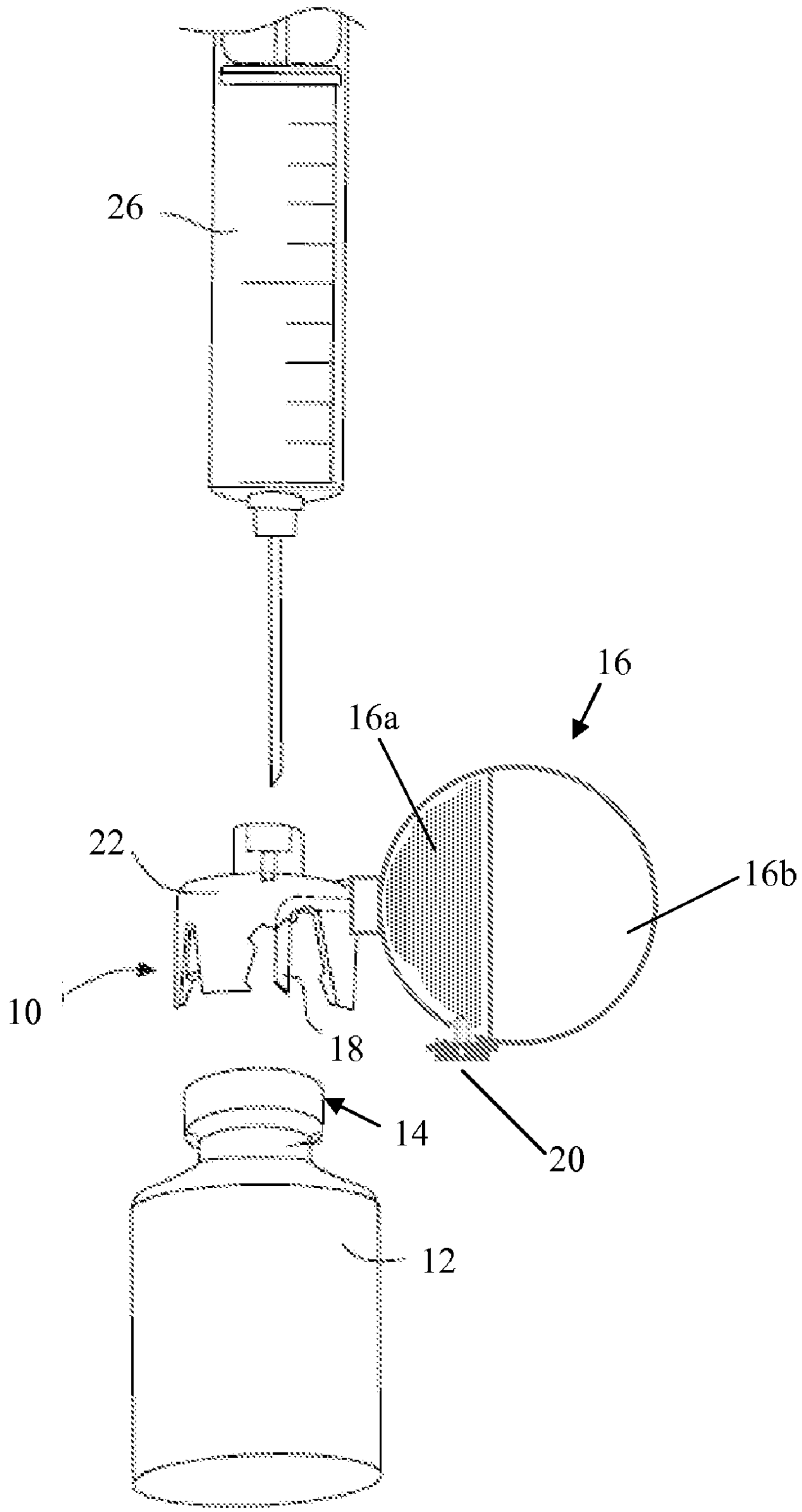
FIG. 1 shows a pressure equalizing device according to an embodiment of the invention prior to attachment to a vial.

FIG. 1 shows a pressure equalizing device 10 according to an embodiment of the invention prior to being attached to a vial 12 containing a solid, liquid or gaseous pharmaceutical, biological or veterinary substance. The vial 12 is sealed by means of a cap 14 and/or an elastomeric stopper or membrane. The pressure equalizing device 10 comprises a gas container 16 having a variable volume. The gas container 16 comprises a first portion 16*a*, such as a plastic parabola coupled to the main body of the pressure equalizing device 10, which comprises a relatively rigid material and a second portion 16*b* comprising a relatively flexible material, such as a thin, transparent plastic film that is attached to the first portion 16*a* in a gastight manner. For example, the gas container 16 can be designed as a bellow which is compressible and extendable. The volume of the gas container 16 can thereby be increased and decreased. Although the device illustrated in FIG. 1 comprises a partly compressible gas container 16, in another embodiment of the invention the gas container 16 can comprise a cylinder and a piston arranged therein so as to enable the volume of the gas container to be changed.

Alternatively, the gas container 16 could be constituted by bellows that are manually expandable and contractible. The gas container 16 illustrated in FIG. 1 is shown in a fully inflated state. The thick dotted line in FIG. 2 illustrates the position of the flexible portion 16*b* when the gas container 16 is in an evacuated and thus fully deflated state.

The gas container 16, which may have a volume of 1 $cm^3$ or less, up to 1 liter or more, depending on the application or size of the receptacle, comprises at least one gas inlet 20 containing a one-way valve and filter-receiving means. The pressure equalizing device 10 comprises connecting means 22, such as a snap fit mechanism for attaching the pressure equalizing device 10 to the neck of a vial 12, which is 1-4 cm in diameter for example and a volume of 50 $cm^3$, whereby the volume of the gas container may be 50 $cm^3$ in its fully inflated state. The pressure equalizing device 10 may of course be dimensioned to be attached to receptacles of any size and volume. The pressure equalizing device 10 also comprises a flow channel 18 that is arranged to provide gas communication between the gas container 16 and the interior of the vial 12 when the pressure equalizing device 10 is connected to the vial 12. FIG. 1 also shows a syringe 26 that may be used to inject fluid into the vial 12 or to withdraw fluid therefrom.

Figure 2:
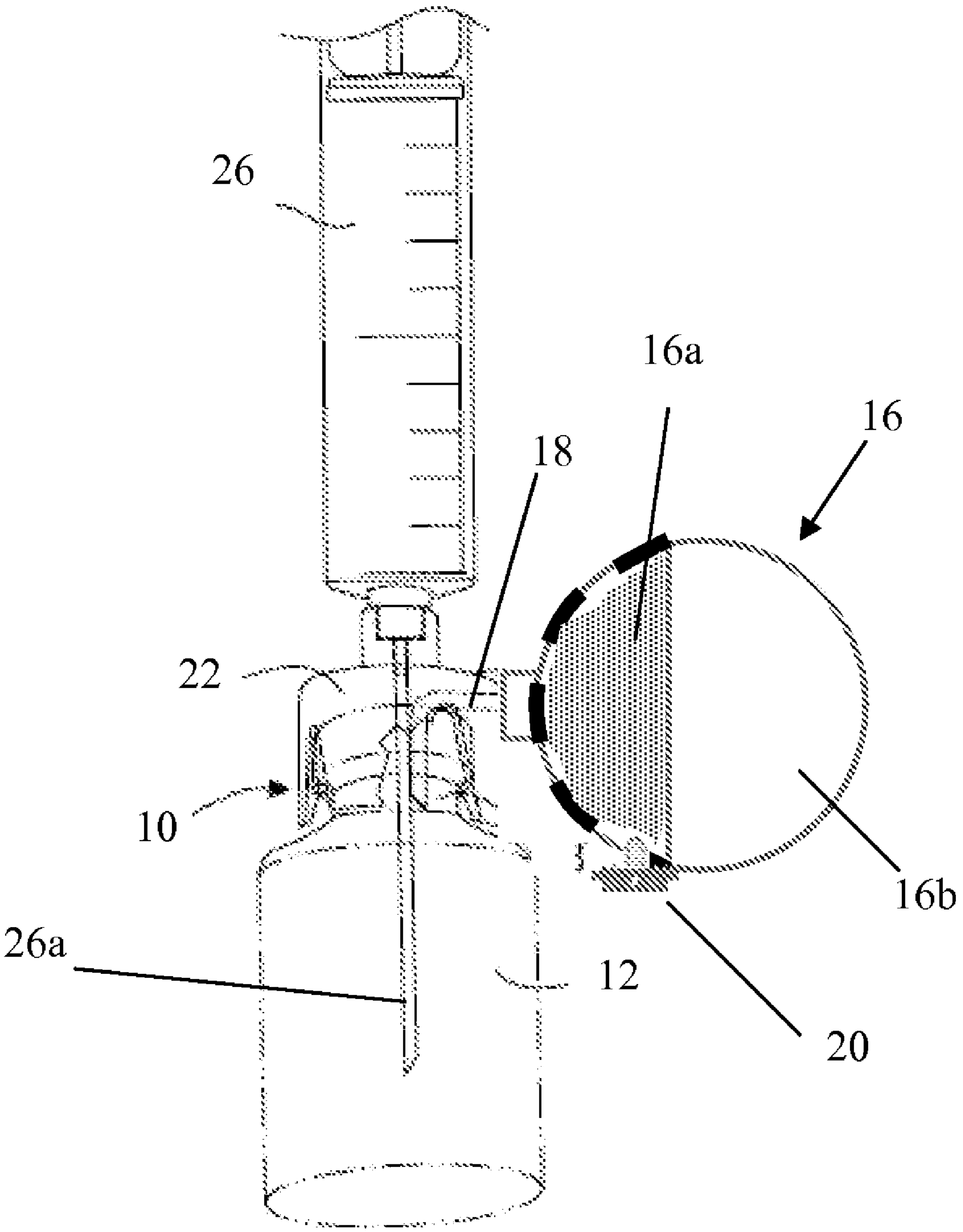
FIG. 2 shows a pressure equalizing device according to an embodiment of the invention, after attachment to attachment to a vial.

FIG. 2 shows the pressure equalizing device 10 shown in FIG. 1 when it has been detachably or non-detachably attached to the vial 12 and when the needle 26*a* of the syringe 26 has been inserted through the pressure equalizing device 10 into the interior of the vial 12. As the fluid is injected into the vial 12 or withdrawn from the vial 12, the flow channel 18 of the pressure equalizing device permits gas to flow from the interior of the vial 12 into the gas container 16 or from the gas container 16 to the vial 12, and thereby equalizes the pressure in the interior of the vial 12 and in the gas container 16. Gas may enter the gas container 16 via the fluid inlet 20, however gas cannot exit the gas container 16. This eliminates, or at least reduces the risk of any substance inside the vial 12 being released into the atmosphere in gas form or by way of aerosolization during the insertion or withdrawal of the needle 26*a* from vial 12 or while the needle 26*a* is inserted in the vial 12. It also eliminates, or reduces the risk of the vial 12 deforming due to the increased pressure inside the vial 12, whereby such deformation may cause leakage of the vial's contents due to separation of the vial's cap 14 from the vial's walls for example.

Figure 3:
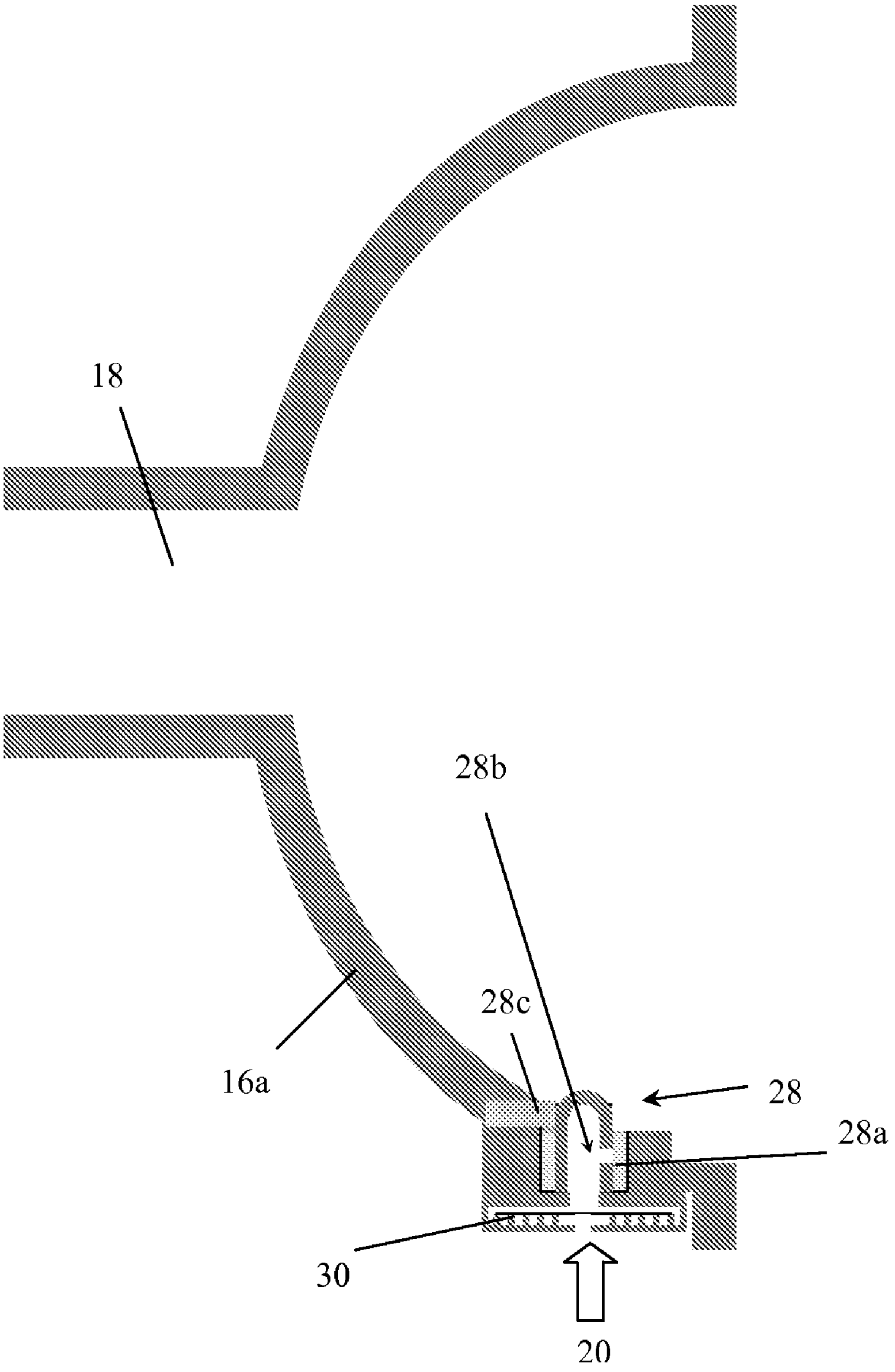
FIG. 3 shows part of a fluid container according to a first embodiment of the invention.

FIG. 3 shows the rigid, incompressible part 16*a* of the gas container 16 shown in FIGS. 1 and 2. This part 16*a* of the gas container comprises the gas inlet 20 that contains a one-way valve 28 that permits gas to flow into the gas container 16 via the gas inlet 20 and that prevents gas from flowing out of the gas container 16 via the gas inlet 20. The gas inlet 20 also comprises filter-receiving means 30 that are located upstream of the one-way valve 28. The gas inlet 20 is arranged to be in communication with ambient air. When a filter is placed in the filter-receiving means 30 ambient air is filtered as it flows into the gas container 16. The filter may be any suitable commercially available filter, such as a particulate air filter having a pore size of 0.2 μm. In the illustrated embodiment the one-way valve 28 is integrally formed with filter-receiving means 30. This integrated unit may be detachable or non-detachable from the gas container 16. The gas container 16 also comprises a flow channel 18 that provides a gas communication channel into and out of the gas container 16.

The embodiment illustrated in FIG. 3 includes an integrated one-way valve 28 and filter-receiving 30 unit that is slidably mounted in the plastic parabola 16*a* of the gas container. The one-way valve 28 comprises an elastic sheath 28*a* that is arranged to cover an opening 28*b* and to uncover the opening 28*b* in its open position. When the pressure outside the gas container 16 exceeds the pressure inside the gas container 16, the integrated one-way valve 28 and filter-receiving means 30 unit is pushed radially inwards in a direction towards the interior of the gas container 16, which causes the elastic sheath 28*a* to abut against a stopper 28*c* and retract, uncovering the opening 28*b* and allowing filtered air into the gas container 16. Conversely, when the pressure inside the gas container 16 exceeds the pressure outside the gas container 16 the integrated one-way valve 28 and filter-receiving means 30 unit is arranged to be pushed radially outwards in a direction out of the gas container 16, whereby the elastic sheath **28*a* extends and covers the opening 28*b* preventing any more gas from entering the gas container 16 via the air inlet 20. The one way valve 28 is arranged to draw ambient air through the filter 30 and out of the opening 28*b* into the gas container 16 when the pressure inside the gas container 16 falls below a predetermined pressure, such as atmospheric pressure in order to keep the pressure inside the vial 12 in equilibrium with the pressure on the exterior of the vial 12. Alternatively, the one way valve 28** could be arranged to be opened and closed manually.

Figure 4:
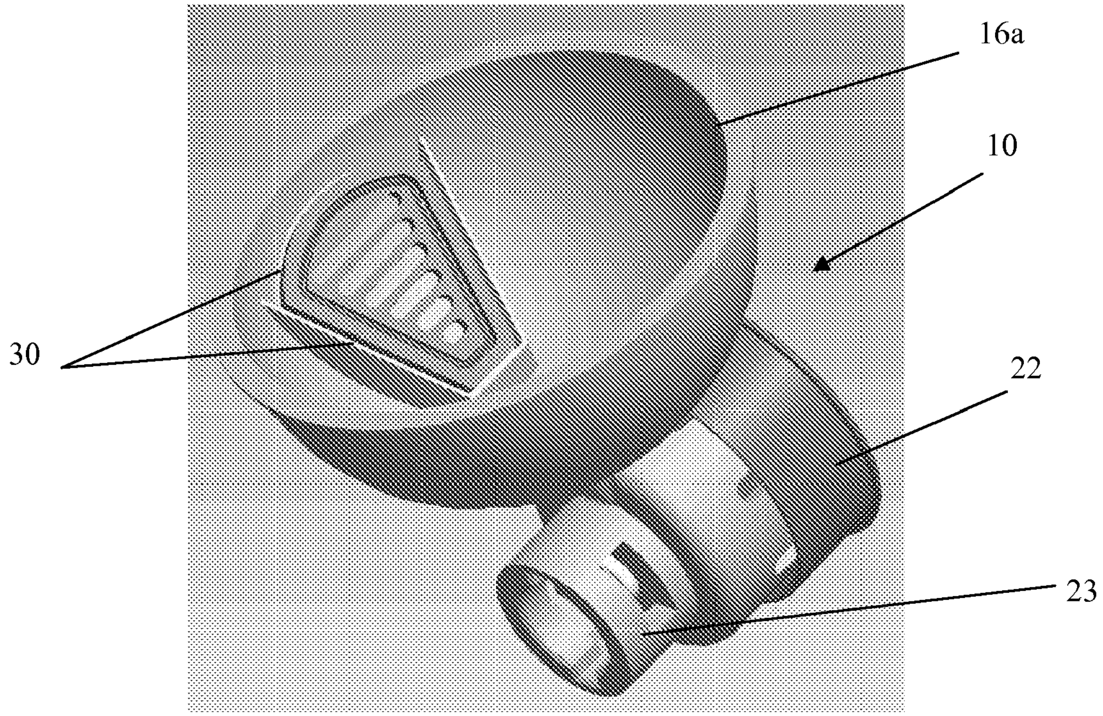
FIGS. 4 & 5 show part of a pressure equalizing device according to a second embodiment of the invention.
Figure 5:
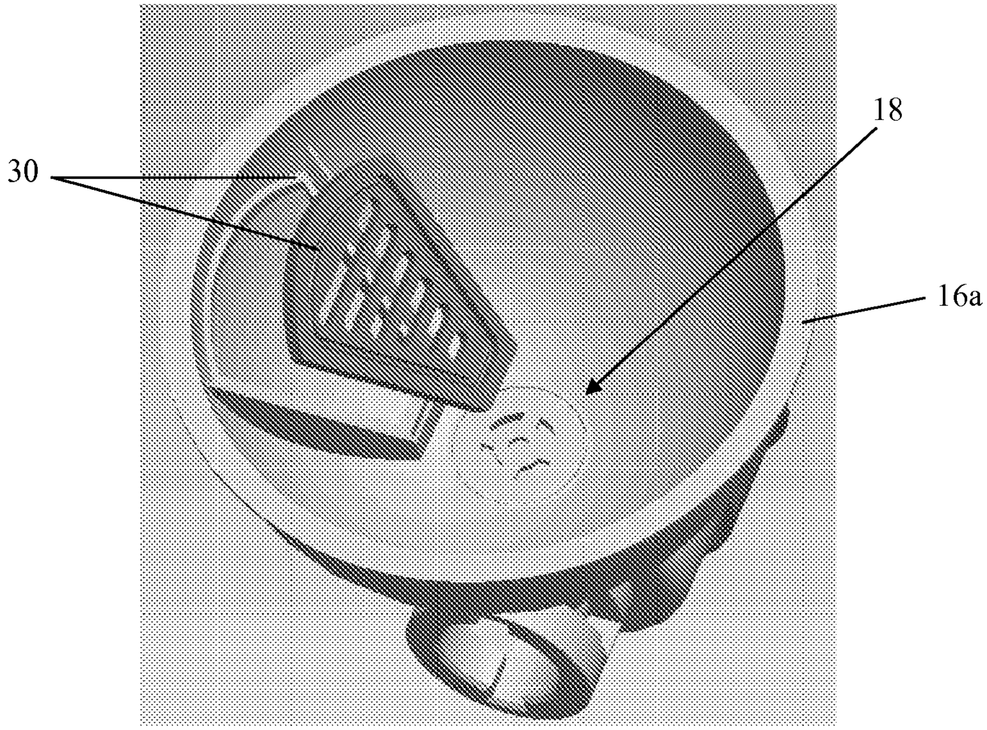

FIGS. 4 and 5 show part of a pressure equalizing device 10 according to a second embodiment of the invention. The pressure equalizing device comprises connecting means 22 for attachment to a receptacle and connecting means 23, namely a bayonet coupling, for attachment to an injector, such as a syringe, and a gas container 16 comprising a plastic parabola **16*a* and a flexible portion (not shown) that is attached to the plastic parabola 16*a*. A filter may be placed in the filter-receiving means 30 to filter gas entering the gas container 16 via the air inlet 20 (that is hidden behind the filter-receiving means 30 in FIGS. 4 and 5**).

The filter-receiving means 30 are either integrally formed with the plastic parabola **16*a* of the gas container 16, by a blow moulding or vacuum forming process for example, or are attached to the inner surface of the plastic parabola 16*a*, by a continuous welding process, such as ultrasound welding, for example. Ultrasound is used to generate internal friction in the plastic of the parabola 16*a* and the filter-receiving means 30 and thereby heat the parabola 16*a* and the filter-receiving means 30. The heated surfaces are then joined together by application of pressure. A filter may be permanently attached to the filter-receiving means 30** using ultrasound welding.

The filter and filter-receiving means 30 should be arranged to ensure that a flexible portion is substantially uniformly inflated so that no part of it is excessively stretched during the inflation thereof. The filter may, for example, be arranged at an angle to the direction of incoming gas as shown in FIGS. 4 and 5, rather than being arranged perpendicularly to the direction of incoming gas. A second filter-receiving means may be placed in the flow channel 18 to enable fluid passing between the vial 12 and the gas container 16 to be filtered.

Figure 6:
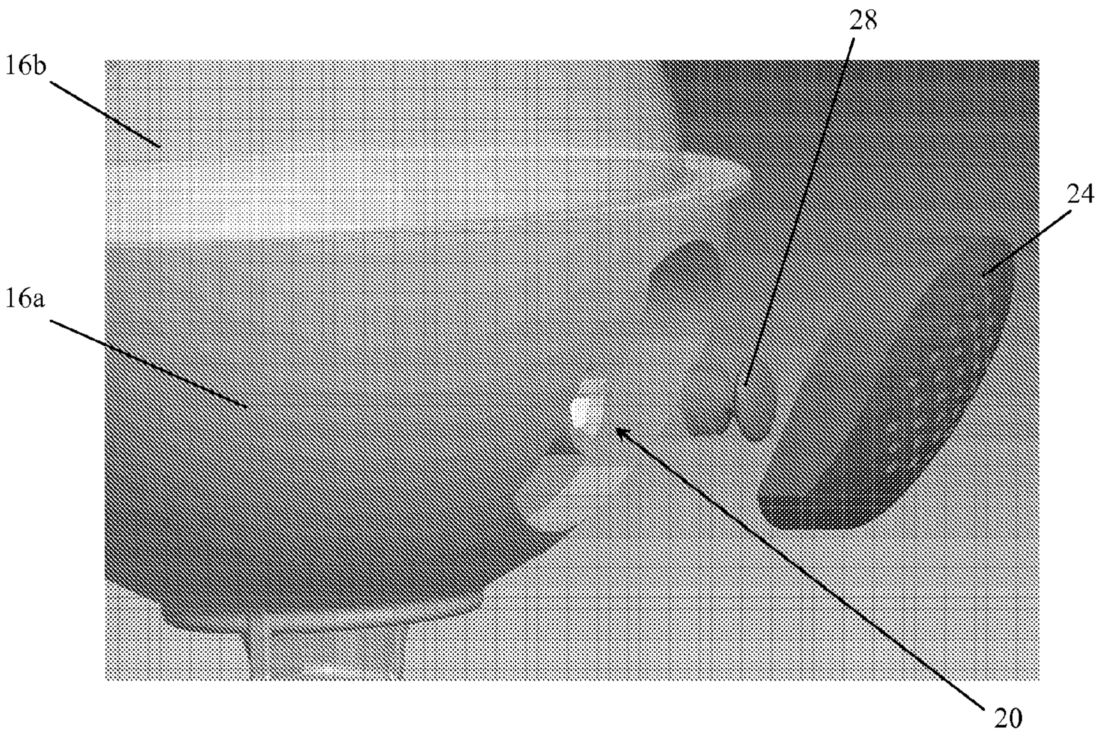
FIGS. 6 & 7 show part of a fluid container according to a third embodiment of the invention.
Figure 7:
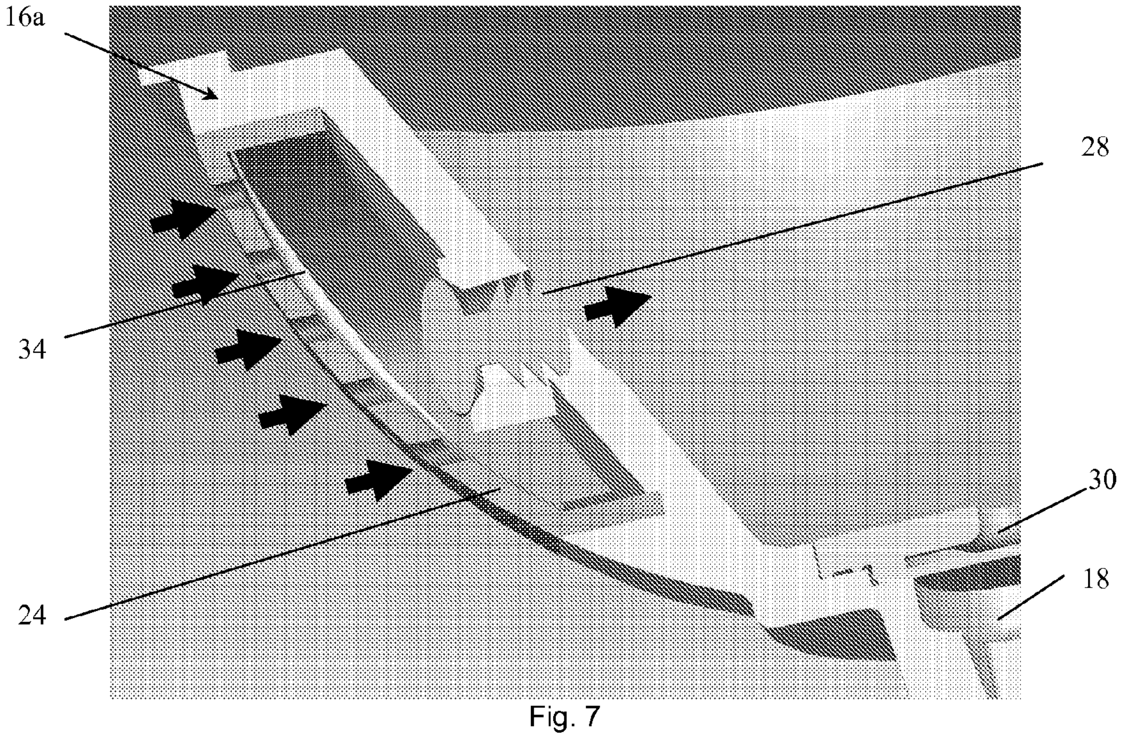

FIG. 6 shows an exploded view of part of a pressure equalizing device 10 according to a third embodiment of the invention. The gas container 16 comprises a parabola **16*a* and a flexible portion 16*b* comprising a thin transparent film. The gas container 16 comprises an air inlet 20 and a one-way valve 28 is located in the air inlet 20. FIG. 7 shows the pressure equalizing device 10 of FIG. 6 when in use. Gas flows into the gas container 16 in the direction of the arrows in FIG. 7, namely through the openings in part 24 of the gas container 16, through a filter 34 into the air inlet 20 via radial channels and past the one-way valve 28 into the interior of the gas container 16. The part 24 comprising the openings in the illustrated embodiment may be arranged to be removable from the gas container 16 or it may be fixedly attached thereto, by means of adhesion or welding for example. FIG. 7 shows that filter-receiving means 30 may be placed at the mouth of the flow channel 18 that provides gas communication into or out of the gas container and/or at any other position along the flow channel 18**.

Figure 8:
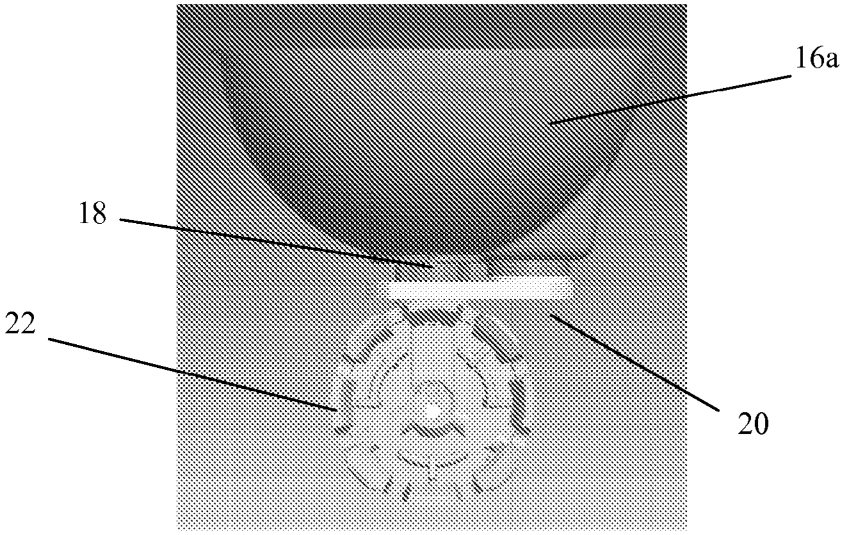
FIGS. 8-10 show part of a pressure equalizing device according to a fourth embodiment of the invention.
Figure 9:
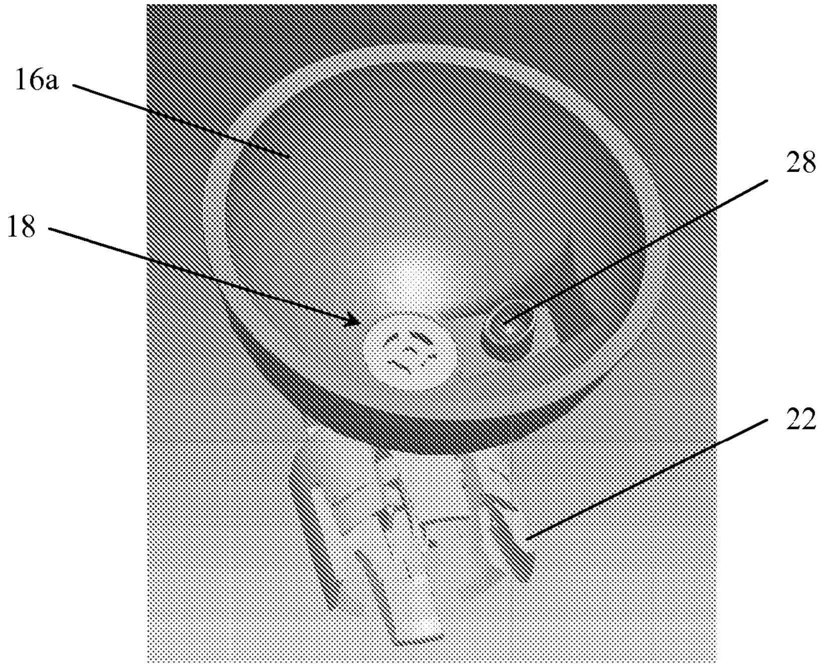
Figure 10:
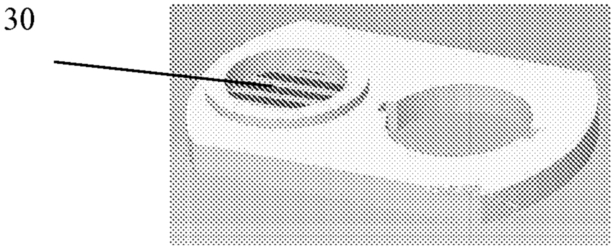

FIGS. 8-10 show part of a pressure equalizing device 10 according to a fourth embodiment of the invention. The pressure equalizing device 10 comprises a gas container comprising a parabola **16*a* and means 22 for connecting the pressure equalizing device 10 to an receptor. The gas container 16 may be detachable from the connecting means 22. The gas container 16 is for example attached to the connecting means 22 by means of a bayonet coupling or any other releasable coupling means. Filter-receiving means 30 are placed in between the gas container 16 and the connecting means 22**.

Figure 11:
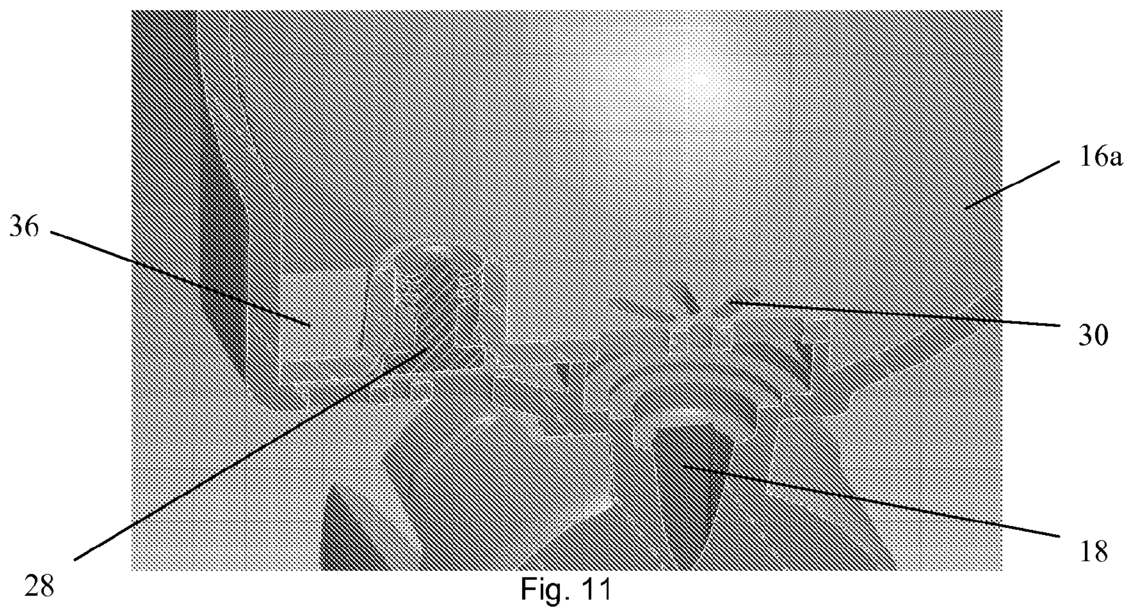
FIGS. 11-13 show part of a pressure equalizing device according to a fifth embodiment of the invention.
Figure 12:
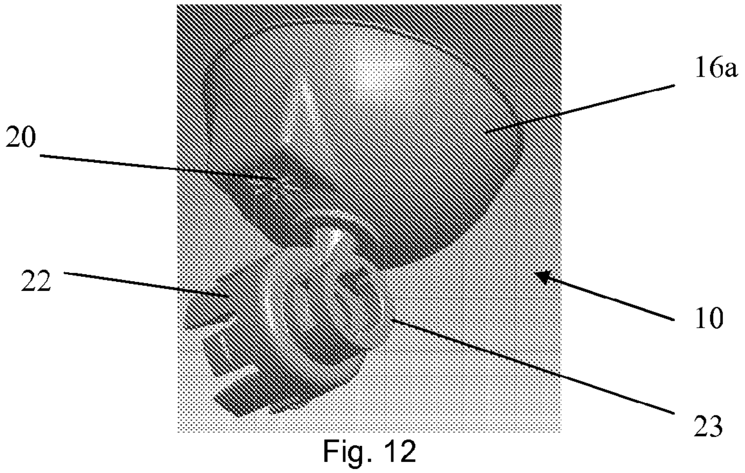
Figure 13:
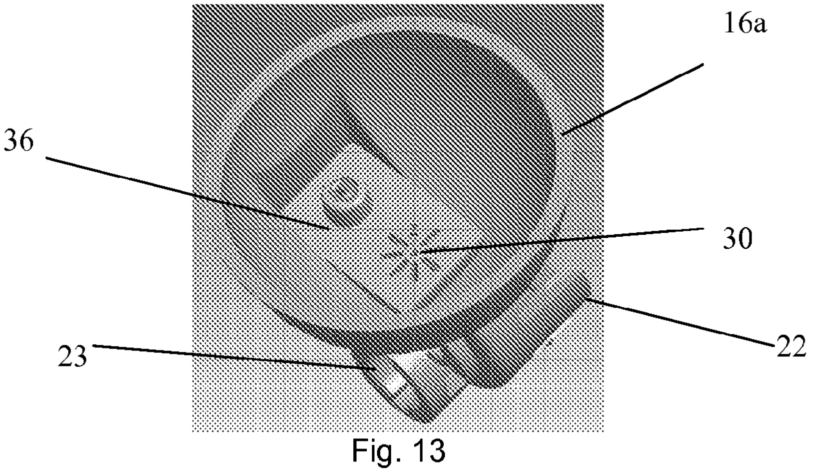

FIGS. 11-13 show part of a pressure equalizing device 10 according to a fifth embodiment of the invention. The pressure equalizing device 10 comprises a parabola **16*a* and connecting means 23 for attaching the pressure equalizing device 10 to an injector, such as a syringe. The parabola 16*a* is integrally formed with the connecting means 22 and 23 in the illustrated embodiment. The pressure equalizing device 10 comprises an insert 36 comprising filter-receiving means 30 and a one-way valve 28. The insert 36 is removably or non-removably attached to the inside of the parabola 16*a* and may be provided with guiding means, to facilitate positioning of the filter-receiving means 30 in the flow channel 18 and/or the one-way valve 28 in the air inlet 20**.

Further modifications of the invention within the scope of the claims would be apparent to a skilled person. For example, the gas container may be of any shape and size and may be located in any suitable position with respect to a receptacle when a pressure equalizing device is attached to a receptacle.

The invention claimed is:

1. A system comprising a receptacle and a pressure equalizing device, wherein said pressure equalizing device comprises:

(a) a fluid container attached to said receptacle and configured to permit pressure equalization between said fluid container, said receptacle, and the ambient environment, (b) a flow channel in fluid communication with said fluid container and said receptacle, (c) a fluid inlet arranged to provide fluid communication into said fluid container, wherein said fluid inlet contains a one-way valve configured to permit fluid to flow into said fluid container from the ambient environment via said fluid inlet and to prevent fluid from flowing out of said fluid container to the ambient environment via said fluid inlet, (d) a filter for filtering fluid flowing into or out of said fluid container, and (e) a filter retainer configured to retain said filter.

2. The system of claim 1, wherein said filter is a removable filter, and said filter retainer is configured to retain said removable filter.

3. The system of claim 1, wherein said filter a sterilizing or aseptisizing filter.

4. The system of claim 1 or 2, wherein said filter retainer is located between said one-way valve and said fluid container.

5. The system of claim 1 or 2, wherein said filter retainer is located in said flow channel, such that fluid is filtered as it flows out of said fluid container into said receptacle.

6. The system of claim 1 or 2, wherein said fluid container is an air container.

7. The system of claim 1 or 2, wherein said fluid container comprises a flexible portion.

8. The system of claim 1 or 2, wherein said one-way valve is integrally formed with said filter retainer or said filter.

9. The system of claim 1 or 2, wherein said filter retainer is detachable from said fluid container.

10. The system of claim 1 or 2, wherein said pressure equalizing device comprises a connector configured to attach said pressure equalizing device to said receptacle.

11. The system of claim 10, wherein at least part of said fluid container is integrally formed with said connector.

12. The system of claim 10, wherein said fluid container is detachable from said connector.

13. The system of claim 1, wherein at least part of said pressure equalizing device is integrally formed with at least one component of said receptacle.

14. The system of claim 1, wherein said pressure equalizing device comprises a connector and an injector, wherein said connector is configured to attach said pressure equalizing device to said injector.

* * * * *